United States Patent [19]

Freeman

[11] Patent Number: 5,034,529
[45] Date of Patent: Jul. 23, 1991

[54] PROCESS FOR THE PRODUCTION OF THIOPHOSPHORIC ACID ESTERS OF HYDROXYPYRIMIDINES

[75] Inventor: William A. Freeman, Mobile, Ala.

[73] Assignee: Ciba-Geigy Corporation, Ardsley, N.Y.

[21] Appl. No.: 319,016

[22] Filed: Mar. 3, 1989

Related U.S. Application Data

[63] Continuation-in-part of Ser. No. 187,162, Apr. 28, 1988, abandoned.

[51] Int. Cl.$^5$ ............................................. C07F 9/6512
[52] U.S. Cl. .................................. 544/243; 544/319
[58] Field of Search ......................................... 544/243

[56] References Cited

U.S. PATENT DOCUMENTS

| | | | |
|---|---|---|---|
| 2,520,393 | 8/1950 | Fletcher | 260/461 |
| 2,664,437 | 12/1953 | Fletcher | 260/461 |
| 2,701,259 | 2/1955 | Schrader | 260/461 |
| 2,754,243 | 7/1956 | Gysin et al. | 544/243 |
| 2,938,831 | 5/1960 | Gordon | 167/33 |
| 3,107,245 | 10/1963 | Gaunt et al. | 544/243 |
| 3,107,246 | 10/1963 | Ferguson | 544/243 |
| 3,329,678 | 7/1967 | Curry et al. | 544/243 |
| 3,367,935 | 2/1968 | Curry et al. | 544/243 |
| 3,741,968 | 6/1973 | Haubein | 544/283 |
| 3,792,132 | 2/1974 | Bernhart | 558/100 |
| 3,886,156 | 5/1975 | Hofer et al. | 544/243 |
| 4,012,506 | 3/1977 | Balke et al. | 544/243 X |
| 4,066,642 | 1/1978 | Sury et al. | 544/243 |
| 4,303,652 | 12/1981 | Jones et al. | 544/232 X |
| 4,308,258 | 12/1981 | Okabe et al. | 544/243 X |
| 4,323,678 | 4/1982 | Schilling | 544/243 |
| 4,326,059 | 4/1982 | Gargano et al. | 544/243 |
| 4,898,942 | 2/1990 | Ovadia et al. | 544/243 |

FOREIGN PATENT DOCUMENTS

097451 1/1984 European Pat. Off.
2343931 4/1975 Fed. Rep. of Germany.

OTHER PUBLICATIONS

Research Disclosure, 310114 (Feb., 1990).

Primary Examiner—Diana Rivers
Attorney, Agent, or Firm—Kevin T. Mansfield; Edward McC. Roberts

[57] ABSTRACT

In a process for the production of a thiophosphoric acid ester of formula I

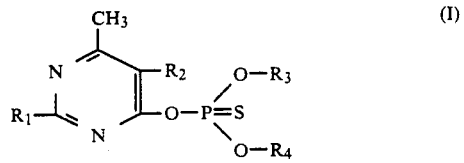

wherein $R_1$ is lower alkyl, lower alkenyl, lower alkoxy(lower)alkyl or lower alkylmercapto(lower)alkyl, $R_2$ is hydrogen, lower alkyl or lower alkenyl and $R_3$ and $R_4$ are lower alkyl, which comprises reacting a dialkyl phosphoric acid halide of formula II

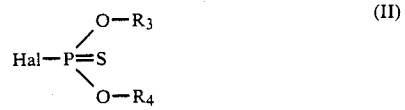

wherein Hal is chlorine or bromine and $R_3$ and $R_4$ are as defined hereinabove, with a hydroxypyrimidine of formula III

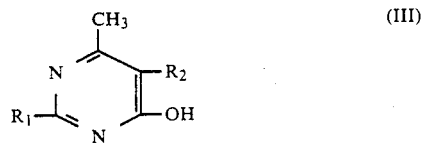

wherein $R_1$ and $R_2$ have the significance given to them above, at elevated temperatures and in the presence of an organic solvent and an acid-binding agent, the improvement which comprises adding the reactant of formula II to an essentially dry mixture of the hydroxypyrimidine of formula III and the acid-binding agent in the presence of a low molecular weight water-insoluble aliphatic or cycloaliphatic ketone as organic solvent after removing the water of reaction from said mixture.

19 Claims, No Drawings

PROCESS FOR THE PRODUCTION OF THIOPHOSPHORIC ACID ESTERS OF HYDROXYPYRIMIDINES

CROSS-REFERENCE

This application is a continuation in-part of copending application U.S. Ser. No. 187,162, filed Apr. 28, 1988, now abandoned.

This invention relates to an improved process of preparing esters of thiophosphoric acid and, more specifically, thiophosphoric acid esters of substituted hydroxypyrimidines.

More particularly, the present invention pertains to the manufacture of esters of dialkoxy thiophosphoric acids of the following general formula:

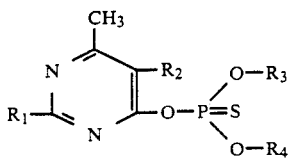

wherein $R_1$ is lower alkyl, lower alkenyl, lower alkoxy(lower)alkyl or lower alkylmercapto(lower)alkyl, $R_2$ is hydrogen, lower alkyl or lower alkenyl and $R_3$ and $R_4$ are lower alkyl. The alkyl and alkenyl groups may be straight chained or branched and have at most 4 carbon atoms.

These compounds, which are disclosed and claimed in U.S. Pat. No. 2,754,243, and especially O,O-diethyl-O-(2-isopropyl-6-methylpyrimidin-4-yl)thiophosphate, are of great commercial value by virtue of their well-established insecticidal and acaricidal activity and consequent usefulness in pest control. Hence there is a strong economic incentive to find more cost-effective routes to their manufacture, for example by increasing the yield, decreasing drying and reaction times and/or decreasing effluent treatment costs. Additionally, as with other important agrochemicals, there is pressure by regulatory agencies to reduce impurity levels in the active substance, particularly the levels of those impurities known to be environmentally objectionable.

According to prior art practices, the compounds of the above formula were initially produced by reacting an aliphatic thiophosphoric acid diester halide of the formula:

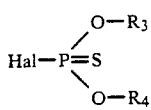

II wherein Hal is chlorine or bromine and $R_3$ and $R_4$ are as defined hereinabove, with a hydroxypyrimidine of the formula:

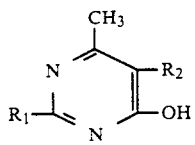

III wherein $R_1$ and $R_2$ have the significance given to them above, in the presence of an inert solvent and an alkali metal carbonate as acid-binding agent.

Benzene, toluene, dioxane and ethyl acetate were all disclosed to be suitable solvents; benzene was exemplified.

However, the practice of such a process entailed certain drawbacks and disadvantages. Thus, for example, it was not commercially feasible to use as acid-binding agent, in lieu of potash, sodium carbonate or sodium hydroxide because the yields were appreciably lower. Even with potash the total reaction time was excessively long from the point of view of commercial feasibility, e.g., in excess of 16 hours.

It was then found that dialkoxy thiophosphates of formula I could be advantageously produced in a considerably shortened period of time by means of a procedure which utilized various catalysts, as for instance, mercury salts, e.g. mercury chlorides and iodides (U.S. Pat. No. 3,107,245) and copper salts, e.g. cupric chloride and cupric nitrate (U.S. Pat. Nos. 3,107,246 and 3,367,935), especially when added to the reaction mixture during the course of refluxing as small aliquots of a solution of the catalyst (U.S. Pat. No. 3,329,678).

However, while these catalytic processes constituted advancements and improvements in the production of the subject dialkoxy thiophosphates, other problems and disadvantages surfaced. It was found that in these processes, e.g., in the conventional and commercial sodium carbonate/copper chloride process, significant amounts of impurities were frequently produced which increase the cholinesterase inhibition activity of these phosphoric acid esters. The presence of the catalyst contributes to the formation of cholinesterase-inhibiting impurities by catalyzing side reactions. In the production of the compound O,O-diethyl-O-(2-isopropyl-6-methylpyrimidin-4-yl)thiophosphate, for example, these impurities are S-TEPP (monothionotetraethylpyrophosphate), SS-TEPP (dithionotetraethylpyrophosphate), the oxo-derivative (which has oxygen in lieu of the sulfur atom of the desired ester) and several others. These specified impurities (S-TEPP, SS-TEPP and oxo-derivative) amounted to 0.5% or more, with the total non-solvent impurity level at 1.5-2.5%. Significant amounts of such cholinesterase-inhibiting impurities are also formed after manufacture due to decomposition of the phosphoric acid esters. (See U.S. Pat. No. 4,066,642 for a further discussion of the cholinesterase inhibition problem). Hence catalysis by heavy metals is no longer practiced. Other patented processes which referred to the reduction of these cholinesterase-inhibiting impurities to less than 0.5% (U.S. Pat. Nos. 4,066,642 and 4,326,059) contained total non-solvent impurities of 1.8-2.4% (4,066,642) or 1.5-2.0% (4,326,059).

Additionally benzene was replaced by toluene or heptane as solvent some time ago because of its oncological properties.

It is the principal object of this invention to produce dialkoxy thiophosphates of formula I of excellent quality and color and in excellent yield.

It is a further important object of this invention to minimize and reduce the formation of undesirable chlorinesterase-inhibiting impurities.

It is a further object to decrease the drying and reaction times.

The above-mentioned objectives can be accomplished by the process of this invention which comprises adding a thiophosphoric acid diester halide of formula II to an essentially dry mixture of a hydroxypyrimidine of formula III and an acid-binding agent, at elevated temperature, in the presence of a low molecular weight water-insoluble aliphatic or cycloaliphatic ketone as organic solvent It is known from U.S. Pat. Nos. 2,520,393, 2,664,437, 2,701,259, 2,938,831, 3,741,968, 3,886,156 and 4,303,652, to prepare other phosphoric acid ester insecticides by carrying out the esterification reaction in a low molecular weight ketone as solvent. In addition to the structural differences of the esters, the yields reported in these patents are all significantly below the ca. 94% presently obtainable for O,O-diethyl-O-(2-isopropyl-6-methyl-pyrimidin-4-yl)-thiophosphate in a hydrocarbon solvent. It is therefore quite surprising and unexpected that both yield and the quality of the thiophosphoric esters of formula I are improved, and in addition the reaction time is decreased, if the reaction of a dialkyl phosphoric acid halide of the formula II with a hydroxypyrimidine of formula III, in the presence of an acid-binding agent, at elevated temperature, is carried out in the presence of a low molecular weight water-insoluble aliphatic or cycloaliphatic ketone as solvent.

Ketones having a solubility in water of less than about 5% at room temperature are considered water-insoluble. Suitable low molecular weight aliphatic ketones are those containing five to eight carbon atoms, preferably five to seven carbon atoms. They may be straight chained or branched. Preferred aliphatic ketones include methyl isopropyl ketone, methyl n-propyl ketone, diethyl ketone methyl n-butyl ketone, methyl isobutyl ketone and methyl n-amyl ketone. Methyl isobutyl ketone is the most preferred aliphatic ketone. By low molecular weight cycloaliphatic ketones is meant those containing a total of five to seven carbon atoms, including any alkyl substituents. Preferred cycloaliphatic ketones are cyclopentanone, 2-methylcyclopentanone, cyclohexanone and 2-methylcyclohexanone, with cyclohexanone most preferred.

The amount of ketone can vary within wide limits. Preferably about 1.5 to 3.0 parts of ketone per part of the pyrimidine on a 100% basis is employed to provide a reasonable compromise between stirrability of the reaction slurry and solvent recovery costs. Most preferably about two parts of ketone per part of hydroxypyrimidine is employed.

The pyrimidines of formula III are known per se. They can be either dried or used directly as a wet cake (25-30% water). Advantageously a 2-20% excess of pyrimidine of formula III is employed relative to the ester chloride, preferably a 6-12% excess.

The acid-binding agent is used in a smaller excess than the pyrimidine of formula III, such as a 1-18% excess, preferably a 4-8% excess. Less expensive acid-binding agents than the potash of the original patent can be advantageously employed in this invention, such as sodium carbonate, potassium hydroxide and sodium hydroxide. The acid-binding agent can be added as a finely divided solid or an aqueous dispersion or solution. Based on cost and ease of handling, 50% aqueous sodium hydroxide is most preferably employed.

In the practice of this invention 1.02 to 1.20 moles of pyrimidine of formula III (dry or wet cake) and 300 to 400 grams of low molecular weight water-insoluble ketone, as previously defined, are combined in a suitable reactor. Said ketone can be fresh or recovered from a previous operation. With agitation 1.01 to 1.18 moles of acid-binding agent is rapidly added and heating is begun. All water is removed by azeotropic distillation, which may be carried out at atmospheric pressure or preferably under vacuum with the higher boiling ketones. When water removal is complete, the temperature is adjusted to 45°-85° C and the thiophosphoric acid diester halide of formula II is added over 15-60 minutes, preferably over 20-40 minutes.

The reaction is accompanied by an adiabatic temperature rise of 30°-40° C. An exotherm to about 100° C. is desirable. Temperatures higher than about 120° C. should be avoided to prevent decomposition of the reactants. This can be readily accomplished by judicious selection of initial reaction temperature and solvent amount, by applying cooling to the reaction mass or by reflux cooling, optionally under vacuum. The reaction mixture is stirred and allowed to cool to about 65° over about one hour. Said reaction mixture is then extracted twice with sodium hydroxide, once with sulfuric acid and once with sodium carbonate solutions. Then the solvent is removed at temperatures up to about 120° C. under high vacuum to afford, in better than 98% typical yield, the thiophosphoric acid ester of formula I which is suitable for use without any further purification as active ingredient for insecticidal and acaracidal preparations.

The invention may be illustrated in greater detail by the following example; it is however not limited thereto.

EXAMPLE 1

Preparation of O,O-diethyl-O-(2-isopropyl-6-methyl-pyrimidin-4-yl)thiophosphate.

To a stirred mixture of 613.5 grams of recovered methyl isobutyl ketone (MIBK) and 405.2 grams of 2-isopropyl-6-methyl-4-hydroxypyrimidine (2.21 moles - 82.9% assay, 11.8% water) in a 5-liter, 4-neck flask equipped with thermometer, blade stirrer, dropping funnel, bottom outlet valve, electric heating mantle, Barret distillate receiver and Friedrich condenser, is added 166.7 grams of sodium hydroxide solution (2.12 moles, 50.9% assay, 48.3% water). The mixture is heated to reflux and azeotropically dried with the MIBK being returned to the flask. Once water removal is complete, the mixture is cooled to about 65° C. Then 381.2 grams of diethylphosphorochloridothioate (2 moles - 98.9% assay) is added over a 30 minute period. The reaction temperature, which increases to about 100° C. by the end of the addition, is permitted to drop to 65° C. during a subsequent 1 hour hold. Then about 260 ml. of water, which may advantageously include the solvent-saturated water removed as an azeotrope earlier, is added and the pH is adjusted to 12.5-13.0 with aqueous sodium hydroxide. After agitating the mixture for 10-15 minutes at 45°-50° C., the agitator is stopped and about 300 ml. of warm water is added. After stirring the mixture slowly for several minutes, the phases are allowed to separate and the lower aqueous phase is discharged. The pH adjustment, water wash and phase separation are then repeated once more.

Then about 340 ml. of water is added to the MIBK solution and the pH is adjusted to 2-3 with sulfuric acid. After the mixture is stirred for 15 minutes at 30°-35° C., the phases are allowed to separate. The lower aqueous phase is discharged and 340 ml. of water is added. While the mixture is stirred, the pH is adjusted to 6.8-7.0 with 10% sodium carbonate solution. After 15 minutes the phases are allowed to separate and the lower aqueous layer is discharged. The wet MIBK solution is then vacuum distilled at up to 118° C. and <1 in. Hg pressure to afford 613.7 grams of 97.7% assay O,O-diethyl-O-(2-isopropyl-6-methylpyrimidin-4-yl)phosphorothioate for a yield of 98.5%. The product contained 0.64% solvent.

A series of 10 consecutive runs was carried out according to the above procedure using recycled MIBK. The results are shown in the following table.

TABLE

| Run No. | Yield, % | Assay, % | MIBK, % | Total IMP, % | Total S-TEPP SS-TEPP, Oxo-Derivative, % |
|---|---|---|---|---|---|
| 1 | 97.0 | 98.0 | 0.73 | 1.3 | 0.20 |
| 2 | 97.8 | 98.3 | 0.64 | 1.1 | 0.17 |
| 3 | 94.9* | 98.3 | 0.66 | 1.0 | 0.10 |
| 4 | 98.0 | 98.1 | 0.59 | 1.3 | <0.10 |
| 5 | 99.3 | 97.9 | 1.06 | 1.0 | 0.10 |
| 6 | 99.1 | 97.5 | 1.53 | 1.0 | 0.13 |
| 7 | 98.9 | 97.9 | 0.82 | 1.3 | 0.12 |
| 8 | 98.5 | 97.7 | 0.64 | 1.7 | 0.13 |
| 9 | 98.5 | 98.4 | 0.59 | 1.0 | 0.10 |
| 10 | 97.3 | 98.2 | 0.63 | 1.2 | 0.08 |
| AVG | 98.3 | 98.0 | 0.78 | 1.2 | 0.14 |

Notes: IMP is all non-solvent impurities.
*Run No. 3 'bumped' during stripping causing the low yield which was not used in the yield average.

What is claimed is:

1. In a process for the production of a thiophosphoric acid ester of formula I

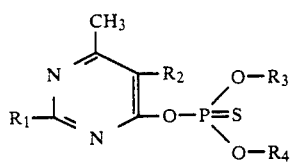
(I)

wherein $R_1$ is lower alkyl, lower alkenyl, lower alkoxy(lower)alkyl or lower alkylmercapto(lower)alkyl, $R_2$ is hydrogen, lower alkyl or lower alkenyl and $R_3$ and $R_4$ are lower alkyl, which comprises reacting a dialkyl phosphoric acid halide of formula II

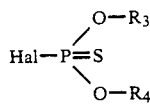
(II)

wherein Hal is chlorine or bromine and $R_3$ and $R_4$ are as defined hereinabove, with a hydroxypyrimidine of formula III

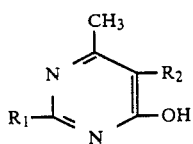
(III)

wherein $R_1$ and $R_2$ have the significance given to them above, at elevated temperatures and in the presence of an organic solvent and an acid-binding agent, the improvement which comprises adding the reactant of formula II to an essentially dry mixture of the hydroxypyrimidine of formula III and the acid-binding agent in the presence of a lower molecular weight water-insoluble aliphatic or cycloaliphatic ketone as organic solvent after removing the water of reaction from said mixture.

2. A process of claim 1, wherein the organic solvent is selected from branched and straight chain $C_5$-$C_8$ aliphatic ketones and cyclic ketones containing a total of 5 to 7 carbon atoms.

3. A process of claim 2, wherein the organic solvent is methyl isobutyl ketone or cyclohexanone.

4. A process of claim 2, wherein there is employed 1.5 to 3 parts of solvent per part of compound of formula III.

5. A process of claim 1, wherein the hydroxypyrimidine of formula III is present in 2-20% molar excess and the acid-binding agent is present in 1-18% molar excess, both relative to the compound of formula II.

6. A process of claim 1, wherein the acid-binding agent is sodium hydroxide.

7. A process of claim 1, wherein the reactant of formula II is O,O-diethyl thiophosphoric acid chloride and the reactant of formula III is 2-isopropyl-6-methyl-4-hydroxypyrimidine.

8. A process of claim 1, wherein 1 mole of O,O-diethyl thiophosphoric acid chloride is added to an essentially dry mixture of 1.06-1.12 moles of 2-isopropyl-6-methyl-4-hydroxypyrimidine and 1.04-1.08 moles of sodium hydroxide, at an initial reaction temperature of 45°-85° C., in methyl isobutyl ketone as organic solvent.

9. A process of claim 1 wherein said acid-binding agent is added to a mixture of said hydroxypyrimidine of formula III in said low molecular weight water-insoluble aliphatic or cycloaliphatic ketone and all water is removed by distillation of the water azeotrope prior to addition of the compound of formula II.

10. A process of claim 1 wherein said acid binding agent is added in the form of an aqueous dispersion or solution.

11. A process of claim 10, wherein the acid binding agent is in the form of about a 50% aqueous sodium hydroxide solution.

12. A process of claim 10, wherein the hydroxypyrimidine of formula III is present in 2-20% molar excess and the acid-binding agent is present in 1-18% molar excess, both relative to the compound of formula II.

13. A process of claim 12, wherein the acid-binding agent is about 50% aqueous sodium hydroxide.

14. A process of claim 10, wherein the reactant of formula II is O,O-diethyl thiophosphoric acid chloride and the reactant of formula III is 2-isopropyl-6-methyl-4-hydroxypyrimidine.

15. A process of claim 13 wherein 1.04-1.08 moles of about 50% aqueous sodium hydroxide is added to 1.06-1.12 moles of 2-isopropyl-6-methyl-4-hydroxypyrimidine in methyl isobutyl ketone as solvent, all water is removed by azeotropic distillation and one mole of O,O-diethyl thiophosphoric acid chloride is added to the essentially dry mixture at an initial reaction temperature of 45°-85° C.

16. A process of claim 1 wherein said acid binding agent is added in the form of a finely divided solid.

17. A process of claim 16, wherein the acid-binding agent is finely divided solid sodium hydroxide.

18. A process of claim 17, wherein the hydroxypyrimidine of formula III is present in 2-20% molar excess and the acid-binding agent is present in 1-18% molar excess, both relative to the compound of formula II.

19. A process of claim 17 wherein 1.04-1.08 moles of finely divided solid sodium hydroxide is added to 1.06-1.12 moles of 2-isopropyl-6-methyl-4-hydroxypyrimidine in methyl isobutyl ketone as solvent, all water is removed by azeotropic distillation and one mole of O,O-diethyl thiophosphoric acid chloride is added to the essentially dry mixture at an initial reaction temperature of 45°-85° C.

* * * * *